(12) United States Patent
Kashwa et al.

(10) Patent No.: US 11,242,231 B1
(45) Date of Patent: Feb. 8, 2022

(54) APPARATUS FOR CONVEYING DELIVERED ITEMS INTO A BUILDING ENVELOPE

(71) Applicants: Adam Kashwa, Highlands Ranch, CO (US); Taylor May Kashwa, Highlands Ranch, CO (US)

(72) Inventors: Adam Kashwa, Highlands Ranch, CO (US); Taylor May Kashwa, Highlands Ranch, CO (US)

( * ) Notice: Subject to any disclaimer, the term of this patent is extended or adjusted under 35 U.S.C. 154(b) by 0 days.

(21) Appl. No.: 17/470,238

(22) Filed: Sep. 9, 2021

(51) Int. Cl.
| | |
|---|---|
| *B66F 7/06* | (2006.01) |
| *B64C 39/02* | (2006.01) |
| *B65G 65/00* | (2006.01) |
| *B65G 69/24* | (2006.01) |
| *G06Q 10/08* | (2012.01) |
| *B65G 47/82* | (2006.01) |
| *A61L 2/10* | (2006.01) |
| *B60W 60/00* | (2020.01) |
| *G05D 1/10* | (2006.01) |

(52) U.S. Cl.
CPC ............ *B66F 7/065* (2013.01); *B64C 39/024* (2013.01); *B65G 47/82* (2013.01); *B65G 65/005* (2013.01); *B65G 69/24* (2013.01); *B66F 7/0666* (2013.01); *G06Q 10/083* (2013.01); *G06Q 10/0832* (2013.01); *A61L 2/10* (2013.01); *A61L 2202/11* (2013.01); *B60W 60/00256* (2020.02); *B65G 2203/0233* (2013.01); *B65G 2203/0258* (2013.01); *B65G 2203/041* (2013.01); *G05D 1/101* (2013.01)

(58) Field of Classification Search
CPC .............................. B66F 7/065; B66F 7/0666
See application file for complete search history.

(56) References Cited

U.S. PATENT DOCUMENTS

| | | | |
|---|---|---|---|
| 1,086,798 A | 2/1914 | Voldsness | |
| 1,400,611 A | 12/1921 | Leger | |
| 2,900,046 A | 8/1959 | Bailey | |
| 2,904,131 A | 9/1959 | Bailey | |
| 3,066,616 A | 12/1962 | Weisberg | |
| 3,785,462 A * | 1/1974 | Coad .................. | B66F 7/065 187/262 |
| 4,941,777 A | 7/1990 | Kieronski | |
| 5,172,791 A | 12/1992 | Couvrette | |
| 6,474,912 B1 | 11/2002 | Meeks | |
| 6,729,808 B1 | 5/2004 | Nelson | |
| 7,077,604 B1 | 7/2006 | Fowler | |
| 9,211,025 B1 | 12/2015 | Elhawwashy | |
| 9,508,239 B1 | 11/2016 | Harrison et al. | |
| 9,990,684 B2 | 6/2018 | Hejazi | |
| 10,026,054 B1 | 7/2018 | Staton et al. | |

(Continued)

FOREIGN PATENT DOCUMENTS

| | | |
|---|---|---|
| AT | 519275 B1 | 10/2018 |
| WO | WO2017173311 A1 | 10/2017 |

*Primary Examiner* — Thomas Randazzo
(74) *Attorney, Agent, or Firm* — Williams Intellectual Property; Benjamin F. Williams

(57) ABSTRACT

An apparatus for conveying delivered items into a building envelope translocates deliveries from a designated receiving area exterior to a building envelope via secure passage onto a deposit area locatable interior to the building envelope. Deposit of an item upon the receiving area signals presence of the delivery. The apparatus is operable automatically via command instantiated in circuit and/or over network in response to the signal.

25 Claims, 16 Drawing Sheets

(56) References Cited

U.S. PATENT DOCUMENTS

| | | | |
|---|---|---|---|
| 10,147,067 B2 | 12/2018 | Pleis | |
| 10,402,774 B1* | 9/2019 | Phillips | G06Q 10/0833 |
| 10,417,603 B2 | 9/2019 | Kosseifi et al. | |
| 10,457,421 B2 | 10/2019 | O'Toole | |
| 10,501,205 B1* | 12/2019 | Siewert | B64F 1/32 |
| 10,817,824 B2 | 10/2020 | Richardson et al. | |
| 10,834,523 B1* | 11/2020 | Rao | G01S 7/4802 |
| 10,860,971 B2 | 12/2020 | Gil et al. | |
| 2011/0052351 A1 | 3/2011 | Voelker | |
| 2014/0014008 A1 | 1/2014 | Tompkins | |
| 2015/0120015 A1* | 4/2015 | Fadell | G06Q 10/0631 |
| | | | 700/90 |
| 2015/0145643 A1* | 5/2015 | Fadell | G07C 9/27 |
| | | | 340/5.51 |
| 2017/0203857 A1 | 7/2017 | O'Toole | |
| 2018/0092484 A1* | 4/2018 | Lewis | A47G 29/20 |
| 2018/0225628 A1* | 8/2018 | Roy | G07C 9/00912 |
| 2019/0039751 A1* | 2/2019 | Janssen | B64C 39/024 |
| 2019/0002129 A1 | 7/2019 | Walsh et al. | |
| 2019/0291961 A1* | 9/2019 | Urban | B64C 39/024 |
| 2019/0343317 A1 | 11/2019 | Cantrell et al. | |
| 2020/0031579 A1* | 1/2020 | Anders | B65G 1/08 |
| 2020/0312068 A1 | 10/2020 | Scalisi et al. | |
| 2020/0364996 A1* | 11/2020 | Sollars | G08B 3/10 |
| 2020/0407079 A1* | 12/2020 | Kim | H02J 50/90 |
| 2021/0045564 A1* | 2/2021 | Duckers | E05F 15/673 |
| 2021/0139294 A1* | 5/2021 | Stehr | B66F 7/0616 |
| 2021/0371128 * | 12/2021 | Rodriguez | B64F 1/20 |

* cited by examiner

APPARATUS FOR CONVEYING DELIVERED ITEMS INTO A BUILDING ENVELOPE

BACKGROUND OF THE INVENTION

Ordering items online for delivery represents an increasing trend in the twenty-first century. Sales online now constitute 14.1% of all retail sales worldwide. See Daniela Coppola, Worldwide e-Commerce Share of Retail Sales 2015-2024, https://www.statista.com/statistics/534123/e-commerce-share-of-retail-sales-worldwide/. Online sales reached $3.5 trillion in 2019. Id. This trend continues apace, eCommerce is expected to reach 21.8% of worldwide retail in 2024. Id. Eight out of ten Americans now shop online. See https://deliverysafe.com/blogs/news/the-ultimate-report-on-package-theft-in-America. Online orders are typically fulfilled by delivery. Purchased items are delivered to the home by couriers, third-party carriers, or mailmen. Larger items that do not fit through mail slots or within mailboxes are typically left near the entrance of the delivery address until the purchaser takes the item(s) inside. This leaves some packages and deliveries susceptible to theft. According to one estimate, 43% of Americans have had a package stolen. Id. Additionally, packages left outside the building envelope may be susceptible to damage caused by inclement or extreme weather.

Means of fulfilling deliveries interior to a building envelope or other secure space typically require a deliverer to place the delivery inside the building envelope or open and deposit the delivery inside a container or securable volume outside the building. This adds time to the delivery process and, where the deliverer opens a part of the building to deposit the delivery, such as interior to a garage or other structure within the property's close, it may raise security concerns.

What is needed is a secure and automated means of translocating a delivery from a position exterior to a building envelope to a position interior to said building envelope. The present apparatus for conveying delivered items into the building envelope, therefore, has been devised to allow a purchaser to remotely activate or, in another embodiment, automate translocation of delivered items from a receiving area outside the building to a deposit area inside the building, and thus remove deliveries into a secure location whether the designated recipient is present in the building or not.

FIELD OF THE INVENTION

The present invention relates to an apparatus for conveying delivered items into a building envelope to enable automated translocation of deliveries from a receiving area outside the building envelope to a deposit area inside the building envelope. The present invention further enables automated and remote control of conveyance whereby a user may verify receipt of a delivery and initiate conveyance into the building via accessing a networked peripheral device.

SUMMARY OF THE INVENTION

The apparatus for conveying delivered items into a building envelope has been devised to enable automated and remotely controllable means of conveying deliveries from a position exterior to a building envelope to the interior of a building envelope.

With the advent of etail and consumer reliance on ecommerce, delivery of items to homes and businesses is increasing with the quantity of goods orderable online. As deliveries to homes and businesses continue to increase, there is a need for a secure means to dispose of delivered items once left outside the building. Further, as ecommerce becomes more and more attractive to consumers worldwide, means to automate fulfillment of items is already being contemplated: Delivery by drone (including unmanned aerial vehicles ("UAVs") and unmanned ground vehicles ("UGVs")), for example, is being explored as a means to meet consumer demand in a cost-effective way. See, e.g., Systems and Methods for Receiving Packages Delivered by Unmanned Vehicles, U.S. Pat. No. 10,026,054 (filed Aug. 4, 2017) (issued Jul. 17, 2018); Drone Docking Station and Delivery System, U.S. Pat. No. 10,457,421 (filed Nov. 21, 2015) (issued Oct. 29, 2019); Methods for Parcel Delivery and Pickup via an Unmanned Aerial Vehicle, U.S. Pat. No. 10,860,971 (filed Dec. 11, 2018) (issued Dec. 8, 2020); and Landing Pad for Unmanned Aerial Vehicle Delivery, U.S. Patent Pub. No. 2019/0002129 (filed Sep. 4, 2018) (published Jan. 3, 2019).

Delivery by drone (including UAVs and UGVs) is desirable because it may decrease delivery times, reduce costs of delivery (and therefore costs of goods to consumers), and increase the efficiency of delivery by, inter alia, lessening the carbon footprint associated with fufillment of orders and the delivery of goods.

The present apparatus for conveying delivered items into a building envelope, therefore, has been devised to safely automate translocation of deliveries into the security of the building envelope while notifying the recipient that the delivery has been made. The present apparatus for conveying delivered items into a building envelope, therefore, includes a designated receiving area situated exterior to the building envelope (such as proximal an entrance to the building, for example, or in a location proximal to where deliveries are typically left at fulfillment by a carrier). The receiving area is contemplated to be demarked in such a manner that it is rendered visible to unmanned aerial vehicles and unmanned ground vehicles, as will be described subsequently, as well as visible to a human carrier. Further, the receiving area is devised to be aesthetically inconspicuous so as to blend in with the surroundings. Nonetheless, an unmanned vehicle or third-party carrier will be able to determine the boundaries of the receiving area whereby deliveries are readily dispatched there. Drop off of deliveries is effectuated in the same manner as is typical, without appreciable change of behavior or process, because the delivery is simply left in the receiving area which is contemplated to be situated proximal the entryway of the delivery address where deliveries are usually left.

Once deposited in the receiving area, the delivery becomes visible within a field of view operative over the receiving area. Sensation of the presence of a delivery may be accommodated by optical apprehension, as by a camera for example, or via other sensing means, such as a light dependent resistor or weight sensor, or other sensor, for example an RFID association between a tag on or in the packaging and the expectation of an order as communicated over network, or a combination thereof, whereby presence of the delivery is signaled. Presence of delivery may be signaled via network to a participating peripheral device. In such embodiments, observation of the receiving area may be monitored via the peripheral device. Initiating the process of conveying the delivery inside the building envelope may also be actuated over network by user action upon the participating peripheral device.

The signal, therefore, instantiates conveyance of the delivery into the building. Conveyance begins when the receiving area is lowered into a first cavity disposed underlying the receiving area. The receiving area is lowered by action of a first lifting means devised to raise and lower the receiving area between an upper and lower position. Once the receiving area reaches the lower position, the delivered item is moved to a conveyance that leads into the building envelope. The conveyance terminates at a second cavity, disposed underlying a deposit area which is movable between a lower position (in close proximity to the conveyance) and an upper position, disposed interior to the building envelope proximal the entrance or place where ingress is typically effectuated.

Movement of the delivery from the receiving area onto the conveyance and to the deposit area may be effectuated by action of an extendible arm configured to move items across the conveyance and onto the deposit area. In such embodiments, the conveyance, then, need not be caused to move the delivery independently, but may comprise a series of rollers, for example, to volubly convey the item to the deposit area. Further, in some embodiments gravity may suffice to translocate the delivery between the receiving area and the deposit area. In other embodiments, the conveyance may be operable to translocate the delivery between the receiving area and the deposit area.

When the receiving area is lowered by the first lifting means into the first cavity, a first cover member may, in some embodiments, be deployed to temporarily cover the first cavity. In at least one embodiment contemplated herein, the first cover member deploys from a recess into an engaged position fitted to the opening vacated by the receiving area. Movement of the first lifting means may trigger action of the first cover member as the lifting means descends and ascends, thereby causing the first cover member to seat into the engaged position and thence return to a retracted position stowed away from the cavity to maintain unobstructed passage of the lifting means. The first cover member may also duplicate the receiving area in such a way that when the receiving area is raised after conveyance of the delivery has removed the delivery from atop the receiving area, the receiving area may detach from the lifting means and stow interior to the recess whereby the first lifting means thence engages with the first cover member which then remains in position in the space vacated by the receiving area at ground or surface level. Thus the first cover member and the receiving area may be interchangeable to ensure that deliveries may be deposited on the receiving area even when the first lifting means is engaged in conveying a previous delivery through the apparatus, as described above.

In such an embodiment, the first cover member deploys into the space vacated by the receiving area as the receiving area is lowered. As the first lifting means thence is raised subsequent removal of the delivery from the receiving area, the first lifting means may detach from the receiving area whereby the receiving area is moved into the recess. The receiving area thence serves as the first cover member as previously described. The first lifting means thence continues to raise to the upper position at which position said first lifting means engages with the first cover member which has now become the receiving area. In like manner, then, the first cavity remains enclosed except for a short interval when the first lifting means is lowering and the first cover member is deployed into the position occupied by the receiving area. This increases security, lessens potential for the intrusion of weather into the first cavity, and maintains continuity of the receiving area for delivery of other packages.

Movement of the first cover member from the recess into the engaged position may be effectuated by action of rails and attachment members that raise the first cover member into the engaged position after the first cover member is presented upon the rails for engagement by the attachment members. In this example embodiment, the attachment members activate once the first cover member is moved from the recess into a position in reach of the attachment members. The attachment members may extend downward via a telescopic rail system disposed on either side of the space vacated by the receiving area. In one example embodiment contemplated herein, deployable hooks (or other attachment mechanisms) may thence deploy to pivotally engage with the first cover member. Once attached, the attachment members may raise the first cover member up to seat into the space vacated by the receiving area. Once positioned into the engaged position, the first cover member thence is positioned to receive incoming packages and serve as the receiving area for receipt of deliveries, as has been previously described.

In at least one embodiment contemplated herein, the apparatus for conveying delivered items into a building envelope may also include a means to sanitize or sterilize deliveries. In such example embodiment, the delivered item is caused to pass through an antimicrobial agent directed at the delivery. Such antimicrobial agent may include bactericides, viricides, disinfectants, fungicides, antibiotics, and other antimicrobial agent, in powdered, mist, or other form, and, in a preferred embodiment, ultraviolet light, or a combination thereof, to disinfect and sanitize the delivery previous to its introduction into the building envelope. The antimicrobial agent is contemplated to be directed at the delivery as the item passes through the first cavity, the conveyance, and/or the second cavity whereby the antimicrobial agent may be targeted at the item within a contained space. The antimicrobial agent prevents exposure to disease and other pathogens such as viruses and bacteria that may inadvertently be vectored into the building envelope with the delivery.

In at least one embodiment contemplated herein, a secure partition may be included to enclose and open at least the second cavity with respect to at least the first cavity. The secure partition is operable to ensure that the second cavity is securely closed off from access form the first cavity until the secure partition is moved to an opened position to accommodate conveyance of a delivery through to the second cavity and deposit area. The secure partition, therefore, operates to prevent unauthorized access into the second cavity (and thus potentially into the building envelope) via the conveyance.

Once the delivered item has been conveyed to the deposit area in the second cavity, in embodiments where an extendible arm is used to translocate the delivery across the conveyance and onto the deposit area, the extendible arm retracts to a recess devised to prevent contact with the first lifting means and receiving area when said first lifting means is in motion toward the upper position.

The deposit area is disposed in operational communication with the second lifting means and is therefore raised from a lower position proximal the conveyance to an upper position proximal a floor level interior to the building envelope. A second cover member, disposed interior to the building envelope, deploys to a stowed position interior to a recess in like manner as the first cover member described above, and allows for the second lifting means to position the deposit area in the space vacated by the second cover member. Removal of the delivered item from the deposit area is sensible to the apparatus and return of the second lifting means to the lower position is operable by means of a signal. Removal of the delivered item may be sensed by means of a field of view or a change in weight sensed upon the deposit area, for example, or by other means, such as the revealing of a light dependent resistor for example. After the delivered item is removed from the second cover member, the signal initiates return of the second lifting means to the lower position. During the descent of the second lifting means, when the deposit area is at a predetermined depth that is clear of the second cover member, the second cover member deploys in like manner as previously described to re-occupy the space vacated by the deposit area.

It is further contemplated that the second lifting means is operable to move between the lower position and the upper position by action of a switch. Said switch may be activated manually or over network. When the switch is activated, either manually or over network, the second cover member stows in like manner as previously described and the deposit area is raised to the space vacated by the second cover member. In like manner as previously described, activation of the switch to another position and/or selection and/or a second time, for example, restores the deposit area to the lower position and reseats the second cover member in position. Thus, the apparatus is operable by manual and remote action independent of the sensors previously described.

Once the second lifting means is returned to the lower position, the apparatus is ready to convey a new delivery interior to the building envelope.

Thus, has been broadly outlined the more important features of the present apparatus for conveying delivered items into a building envelope so that the detailed description thereof that follows may be better understood and in order that the present contribution to the art may be better appreciated.

Objects of the present apparatus for conveying delivered items into a building envelope, along with various novel features that characterize the invention are particularly pointed out in the claims forming a part of this disclosure. For better understanding of the apparatus for conveying delivered items into a building envelope, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
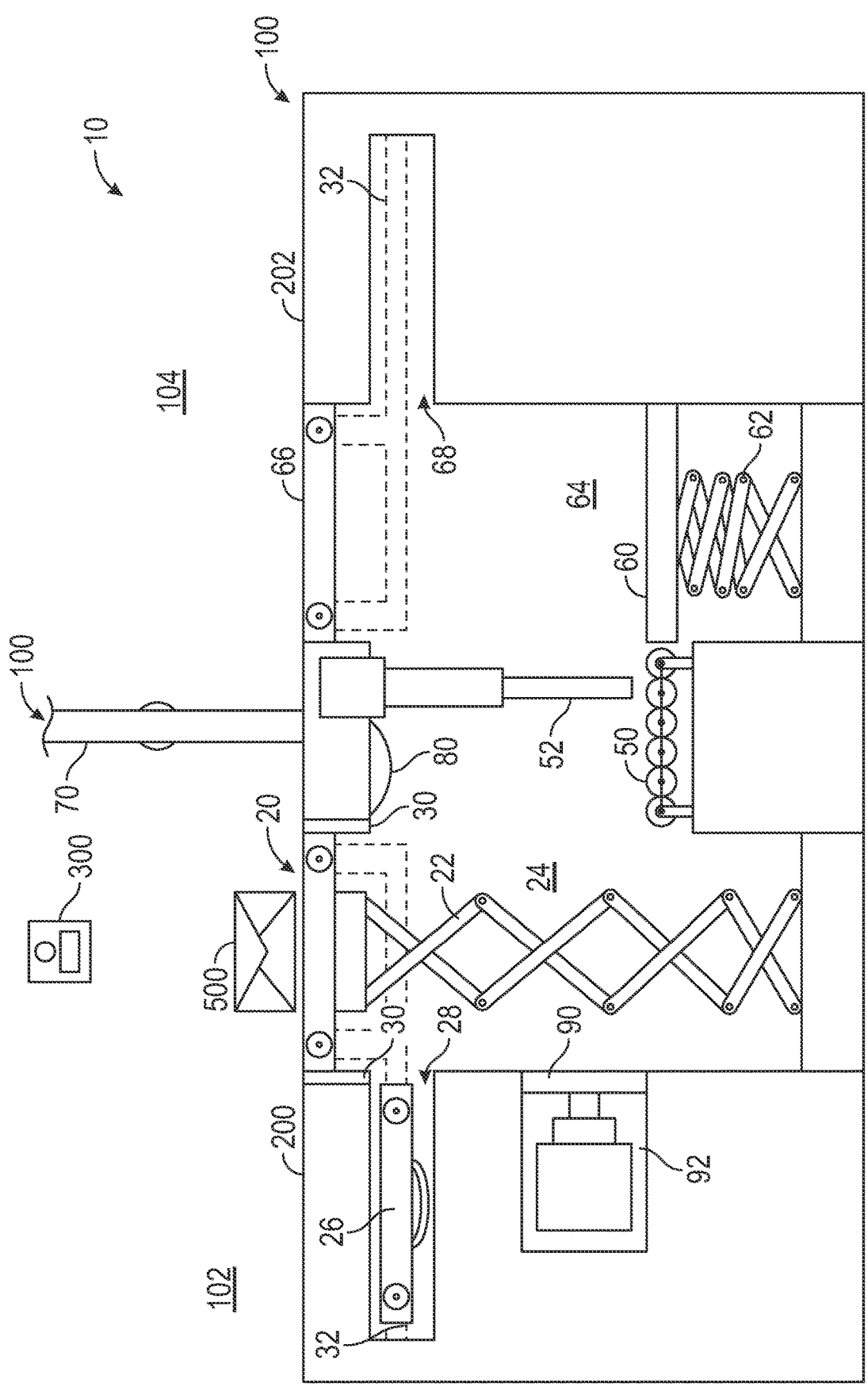
FIG. 1 is a diagrammatic side elevation view depicting an example embodiment of the present invention showing a delivery positioned within a receiving area.

With reference now to the drawings, an example embodiment of the instant apparatus for conveying delivered items 10 into a building envelope is described. It should be noted that the example embodiment depicted and described below is set forth as an example only, to exemplify the principles and concepts informing the general inventive step comprising the invention. Persons of ordinary skill in the art will readily apprehend variations thereof that do not depart from the general scope of the invention. Thus, the examples given herein should not be considered as limiting, but set forth to provide scope to the accompanying claims which, in the broadest reasonable interpretation consistent with the instant disclosure, define the intended metes and bounds of the invention set forth.

FIGS. 1 through 14, therefore, depict a diagrammatic, side elevation view of a preferred embodiment in example configuration. Receiving area 20 is disposed exteriorly relative a building envelope 100. As used herein throughout, the term "building envelope" is taken to mean that portion of a building or structure that partitions the interior space from the exterior environment. Building exterior 102 is therefore represented as exterior to building envelope 100 and building interior 104 is represented as interior to building envelope 100. The envelope 100 thus partitions the inside of the building; and delimits the portion of the building wherefrom others may be excluded. Receiving area 20 is disposed proximal entrance 70 at a location where deliveries are frequently deposited by third-party carriers and, in some cases, unmanned vehicles (including unmanned aerial vehicles and unmanned ground vehicles). In this example embodiment, receiving area 20 comprises a parallelepiped plate presenting a surface area wherein items may be deposited upon delivery. Receiving area 20 is operatively coupled with first lifting means 22. First lifting means 22 is movable between an upper position (presenting receiving area 20 flush with ground surface 200) and a lower position (presenting receiving area 20 proximal to conveyance 50, as will be described subsequently). In this example embodiment, first lifting means 22 is depicted as a scissor lift, however other means of raising and lowering the receiving area 20 between the upper and lower positions is contemplated as within scope of this disclosure.

Figure 15:
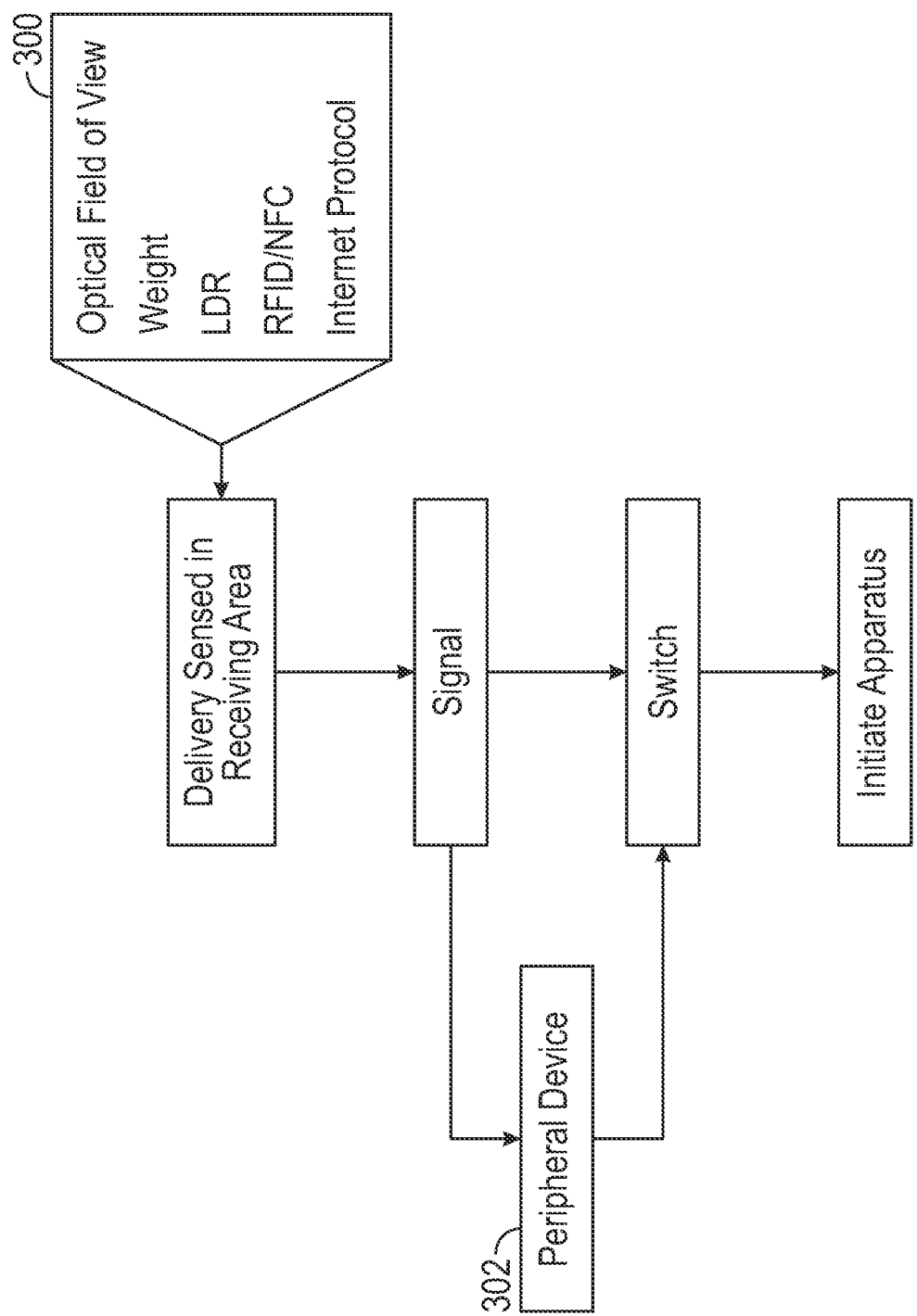
FIG. 15 is a diagrammatic view of a networked peripheral device operative over network to initiate the apparatus to translocate the delivery from the receiving area to the deposit area and from the building exterior to the building interior.

In this example embodiment, deposit of item 500 to receiving area 20 is signaled via sensor 300 (see, e.g., FIG. 15). In a preferred embodiment, sensor 300 is a camera with field of view operative over the receiving area 20. In other embodiments, sensor 300 may include a weight sensor, a light dependent resistor, or other sensing means, or combination of the aforementioned, whereby presence of item 500 within receiving area 20 is determinable. Additionally, where radio identification ("RFID") tags are incorporated into packaging for purposes of tracking delivery, or other near field communication enablement, near field communication ("NFC") may operate to signal association of a particular RFID in receipt of the receiving area 20. Additionally, communications protocol established by the carrier scanning an item to update a delivery status online may communicate to the recipient over network to signal delivery of the item 500 within the receiving area 20. See FIGS. 15 and 16.

When the signal is communicated, first lifting means 22 may be activated over network from a participating peripheral device 302 (see FIG. 15). Alternatively, the apparatus 10 may operate automatically. In any case, when the signal is instantiated, the first lifting means 22 lowers toward the lower position by descending within first cavity 24. As first lifting means 22 descends, first lifting means 22 triggers first cover member 26 to deploy from recess 28 into an engagement position occupying the position of the receiving area 20 flush with ground or other surface 200. See FIGS. 2 and 3. In this example embodiment, first cover member 26 deploys along rails 32 to slidingly position for connection with attachment members 30 that raise first cover member 26 into the engagement position once positioned out from recess 28. Note further, that in this example embodiment, first cover member 26 essentially becomes an alternative receiving area 20 once in the engaged position. Receiving area 20 will thereafter be stowed into recess 28 when first lifting means 22 again ascends toward the upper position after delivery 500 has been conveyed to deposit area 60 as will be described subsequently. See below.

Figure 2:
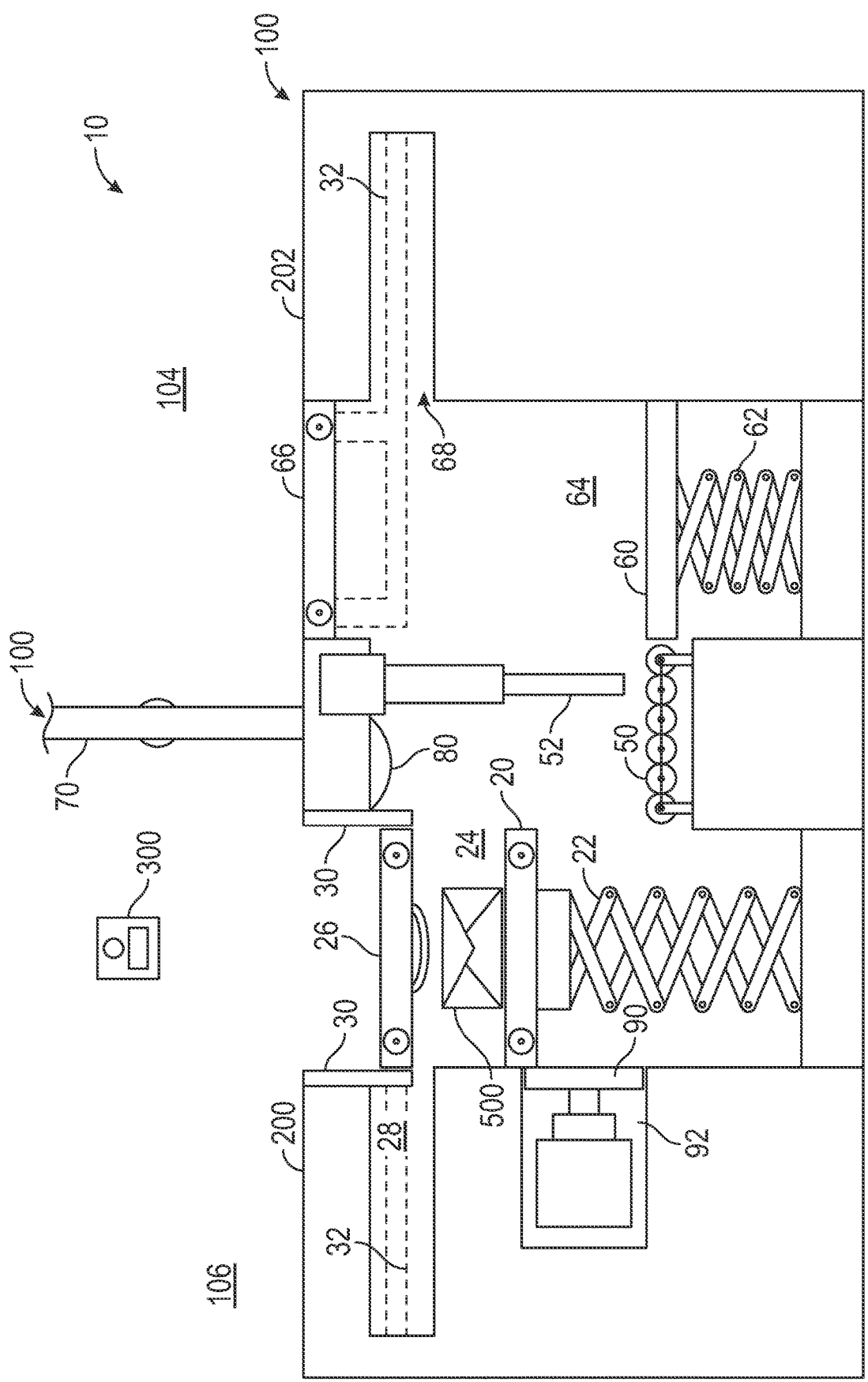
FIG. 2 is a diagrammatic side elevation view depicting an example embodiment of the present invention showing the delivery positioned within a receiving area lowered by action of a first lifting means to a lower position interior to a first cavity.
Figure 3:
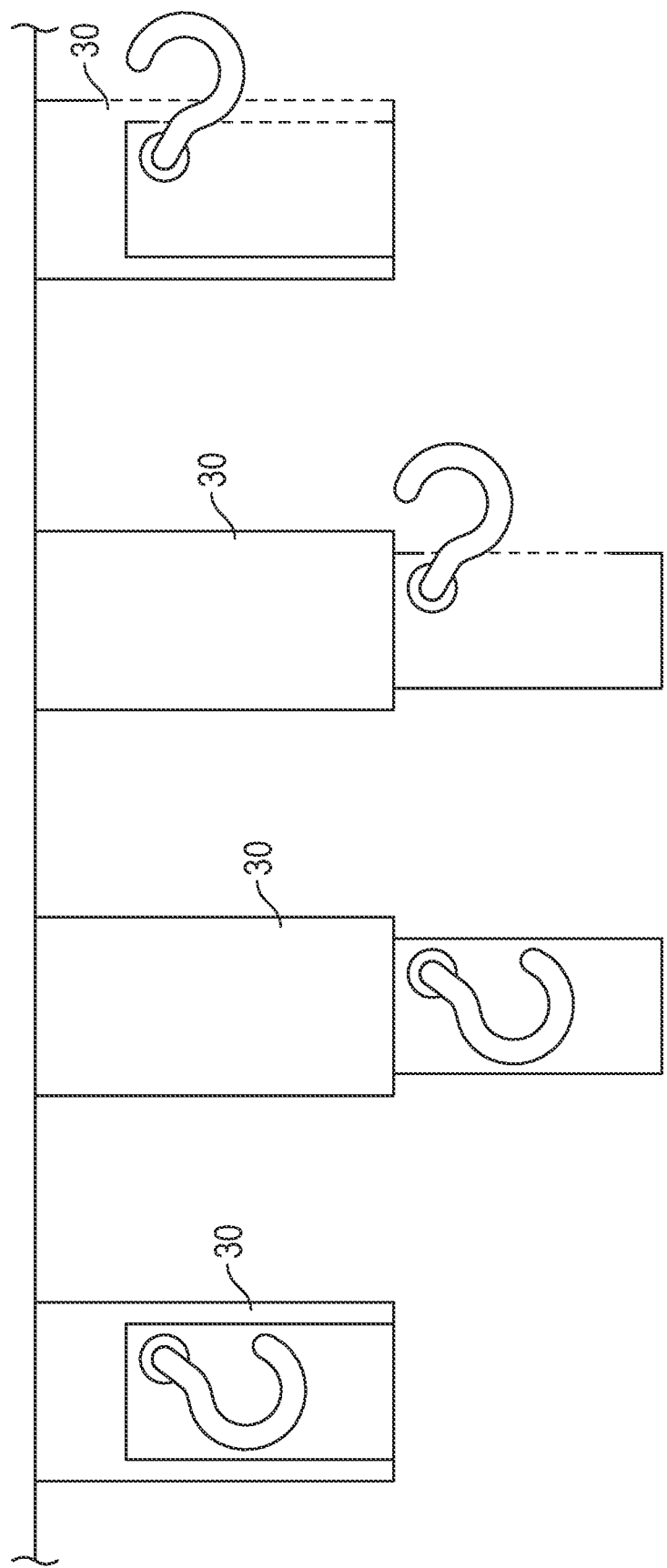
FIG. 3 is a detail side elevation view of an example embodiment of one of a pair of attachment members by which the first cover member is raised into the position vacated by the receiving area.

As shown in FIG. 2, first lifting means 22 descends to the lower position and presents receiving area 20 aligned with conveyance 50. See FIG. 4. As first lifting means 22 descends, first cover member 26 deploys from recess 28. In this example embodiment, first cover member 26 slides along rails 32 and is engaged by attachment members 30 that raise first cover member 26 into the position vacated by receiving area 20. Attachment members 30 are shown in example embodiment in the detail view illustrated in FIG. 3 as hook members, however any effective means of selectively attaching and raising first cover member 26 into the engaged position is contemplated as part of this disclosure. In this particular example embodiment, attachment members 30 telescopically deploy and rotate to engage with the first cover member 26 to position first cover member 20 into the engaged position occupying the space vacated by the receiving area 20. Attachment members 30 may connect with first cover member 26 by any means suitable to supportively uplift the first cover member 26 into the engaged position while allowing for selective detachment of the attachment members 30 once the first cover member 26 is disposed into the engaged position. Essentially, a means of independently raising the first cover member 26 into the engaged position absent action of the first lifting means 22 is contemplated as part of this example embodiment whereby the first cover member 26 effectively replaces the receiving area 20 (and effectively becomes a new receiving area 20) shortly after the first lifting means 22 is lowered.

Figure 4:
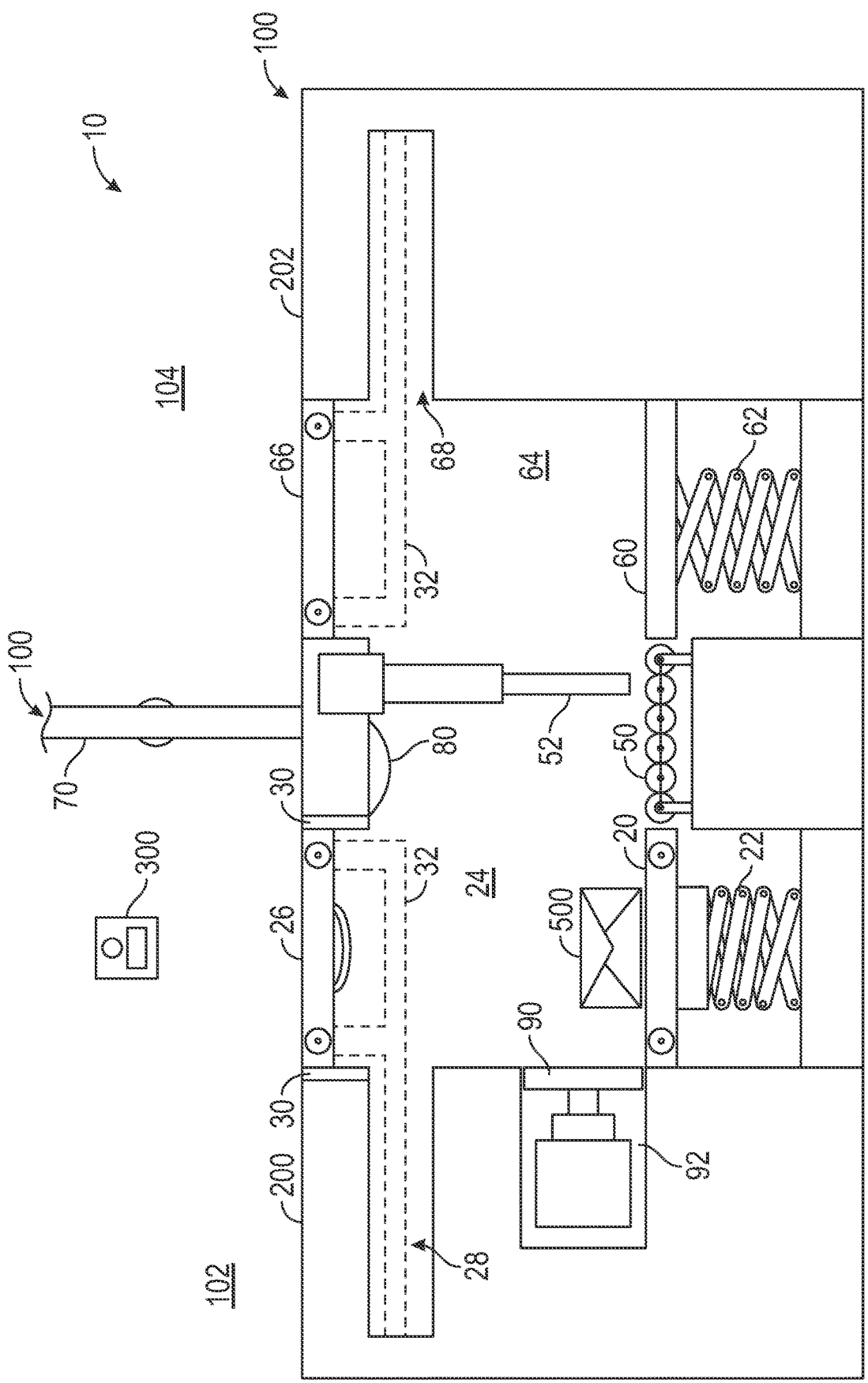
FIG. 4 is a diagrammatic side elevation view depicting an example embodiment of the present invention showing action of a first cover member positioned into an engaged position enclosing the first cavity.
Figure 5:
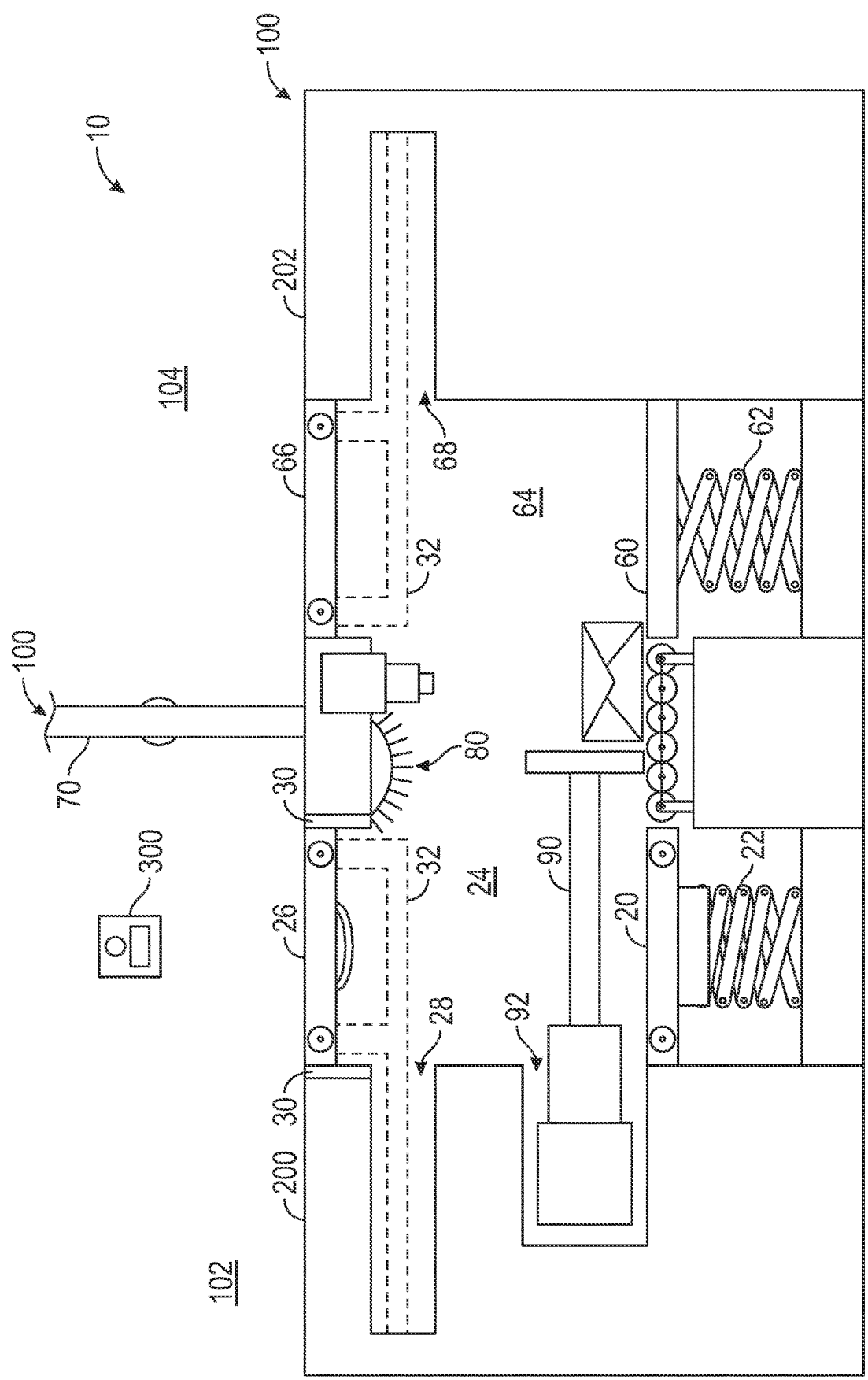
FIG. 5 is a diagrammatic side elevation view depicting an example embodiment of the present invention showing movement of a secure partition from a closed position to an open position to enable access of the delivery across a conveyance onto a deposit area while an antimicrobial agent (here, ultraviolet light) is administered to the delivery.
Figure 6:
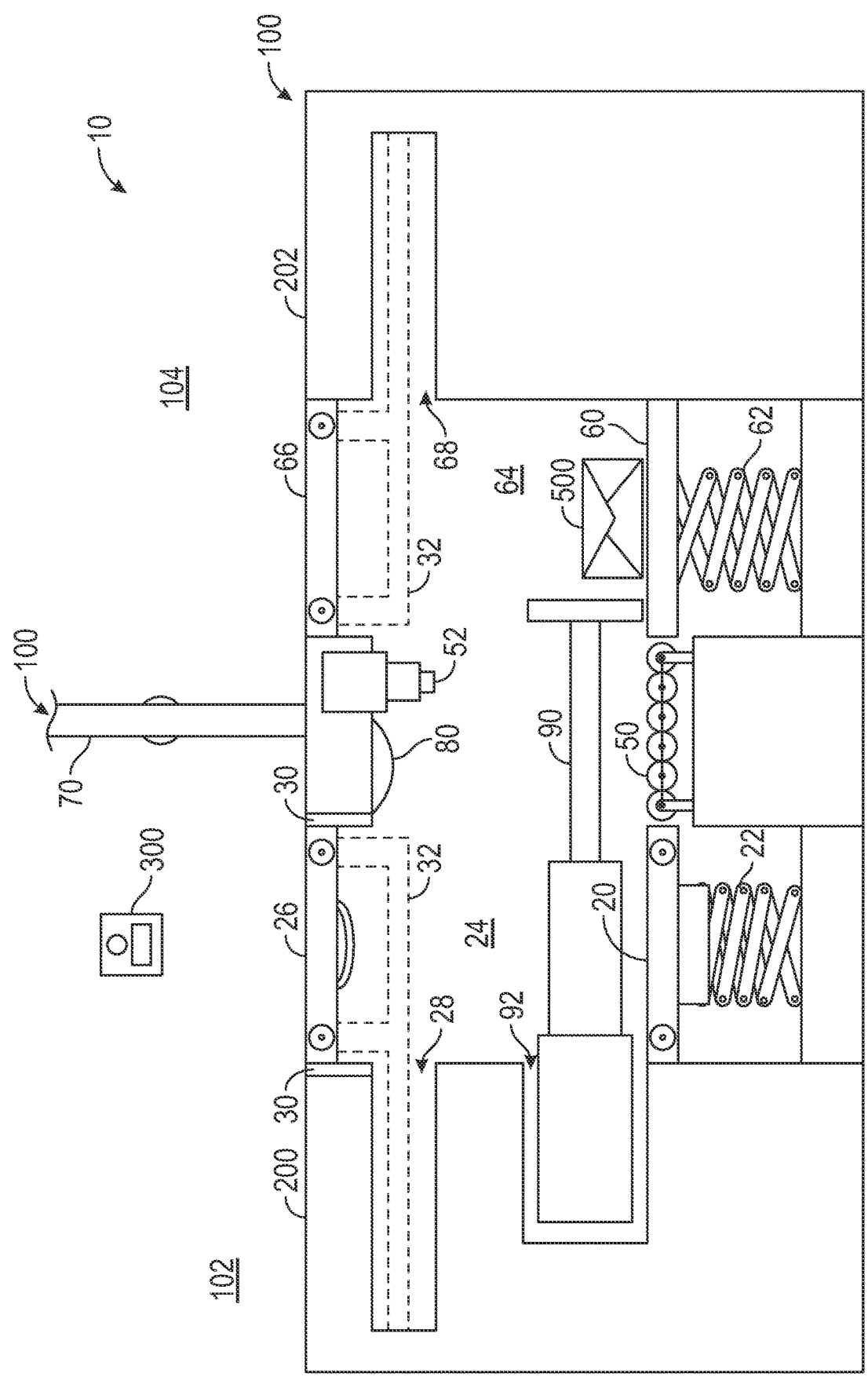
FIG. 6 is a diagrammatic side elevation view depicting an example embodiment of the present invention showing action of an extendible arm translocating the delivery from the receiving area to the deposit area by way of the conveyance.
Figure 7:
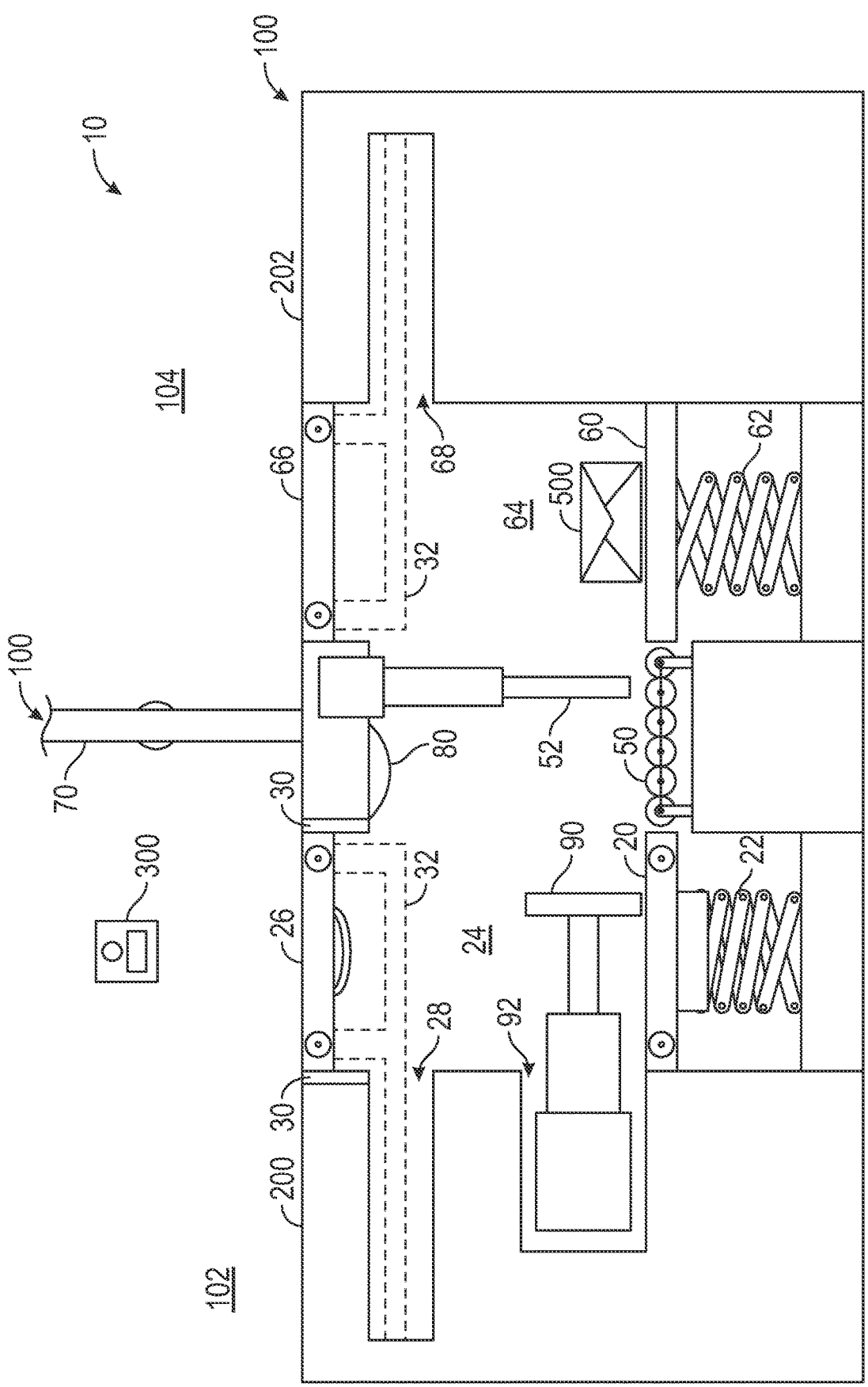
FIG. 7 is a diagrammatic side elevation view depicting an example embodiment of the present invention showing the delivery positioned atop the deposit area for raising into the building envelope. Extendible arm is retracted and the partition is reimposed.

In this preferred embodiment, as shown in FIGS. 4 and 5, seating of first lifting means 22 into the lower position and/or seating of first cover member 26 into the engaged position triggers opening of secure partition 52 which serves to close off second cavity 64 from the conveyance 50 when in the extended or closed position. See FIG. 4. Once the secure partition 52 is opened (see FIG. 5), extendible arm 90 is actuated to extend from recess 92 and move the delivered item 500 across conveyance 50 and onto deposit area 60 disposed atop second lifting means 62. See FIGS. 5 and 6. As the delivery is conveyed across conveyance 50, antimicrobial agent 80 is applied over the delivery. See FIG. 5. In the example embodiment depicted, antimicrobial agent 50 is ultraviolet light. Once extendible arm 90 has reached the extended position, extendible arm 90 retracts into the retracted position interior to recess 92. Secure partition 52 then closes. See FIGS. 7 and 8.

Figure 8:
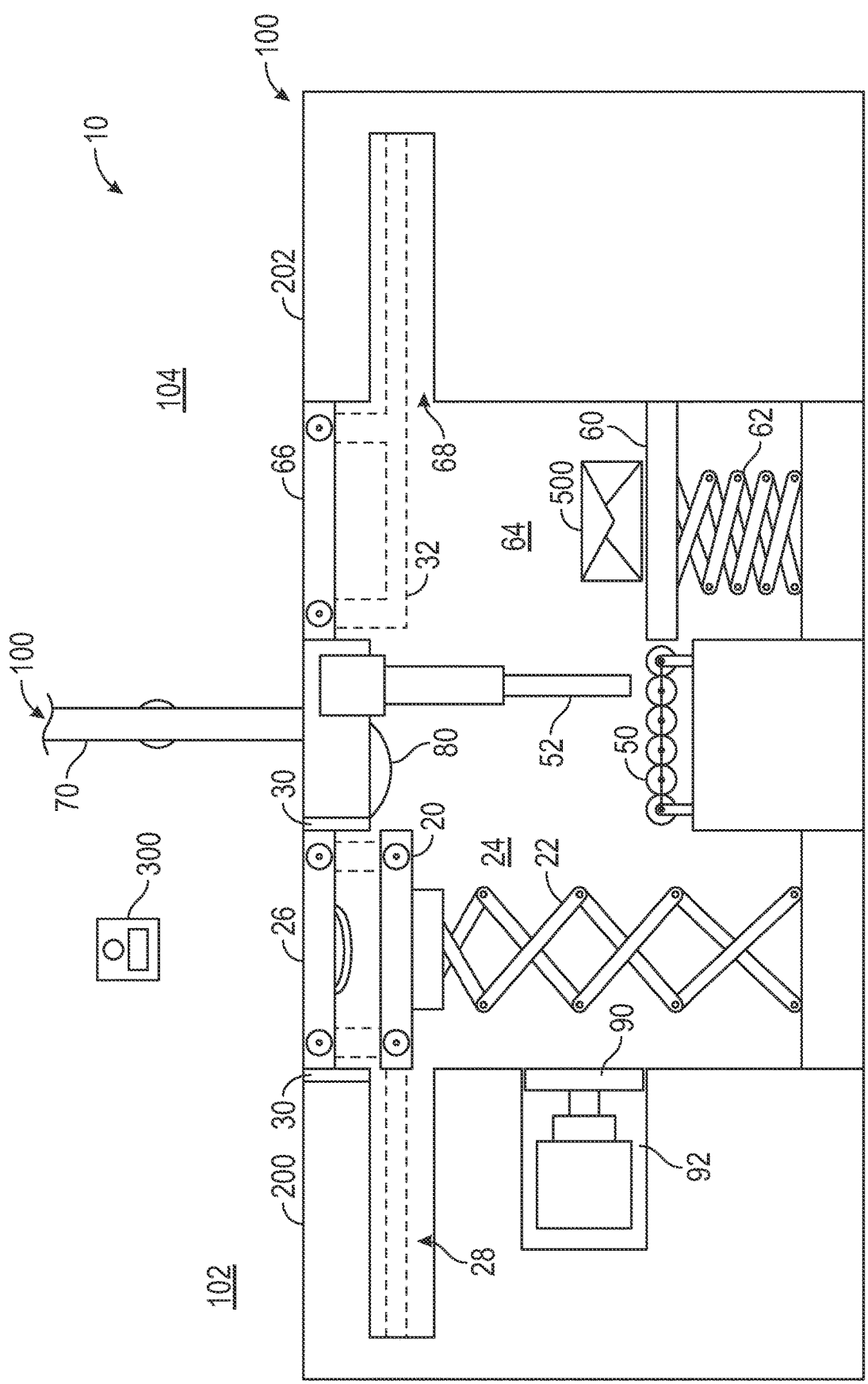
FIG. 8 is a diagrammatic side elevation view depicting an example embodiment of the present invention showing action of the extendible arm returned to a retracted position and illustrating the first lifting means rising toward an upper position whereby the receiving area is detached and positioned into the recess to become the first cover member.
Figure 9:
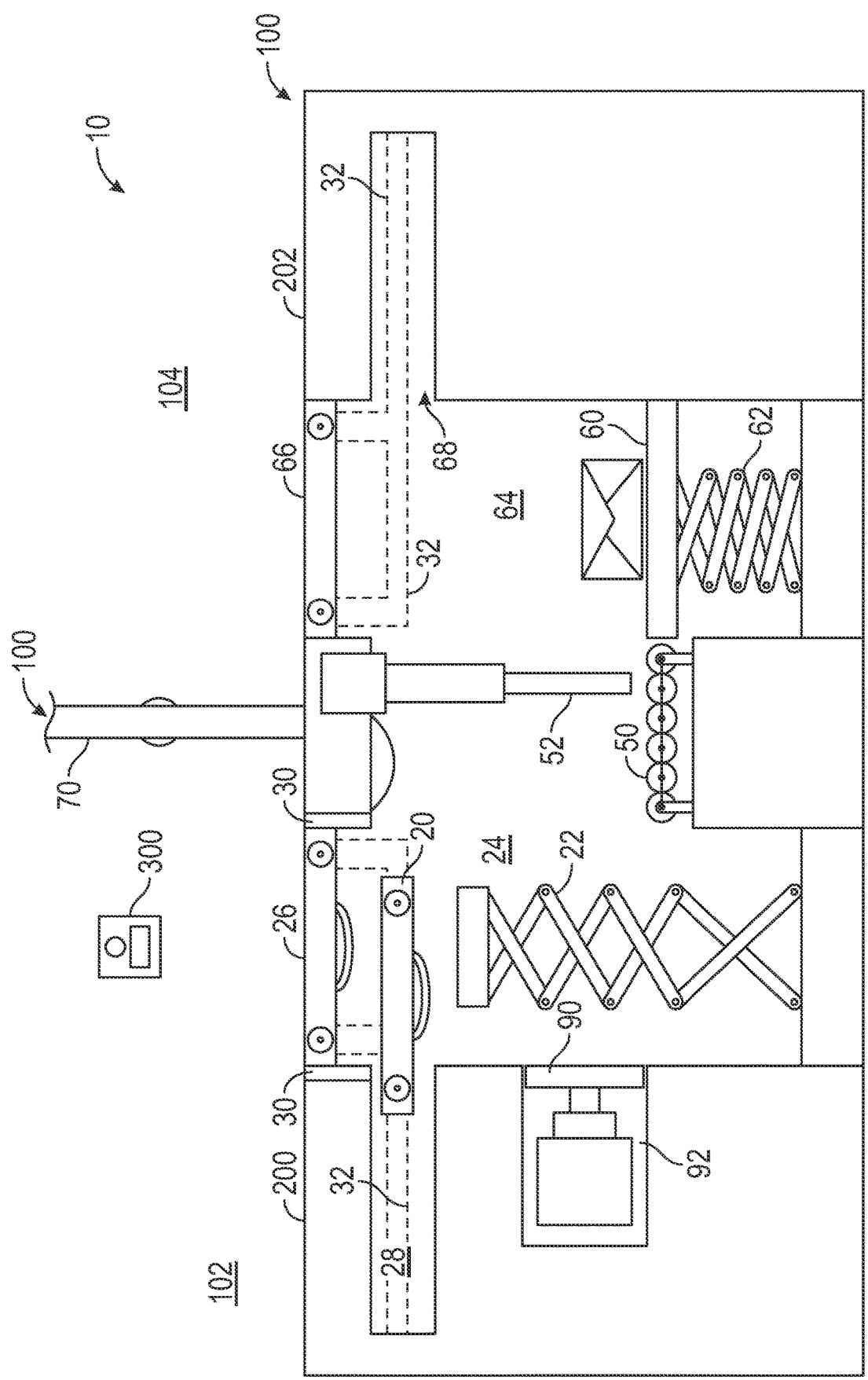
FIG. 9 is a diagrammatic side elevation view depicting an example embodiment of the present invention showing action of the receiving area moving to the stowed position interior to the recess.
Figure 10:
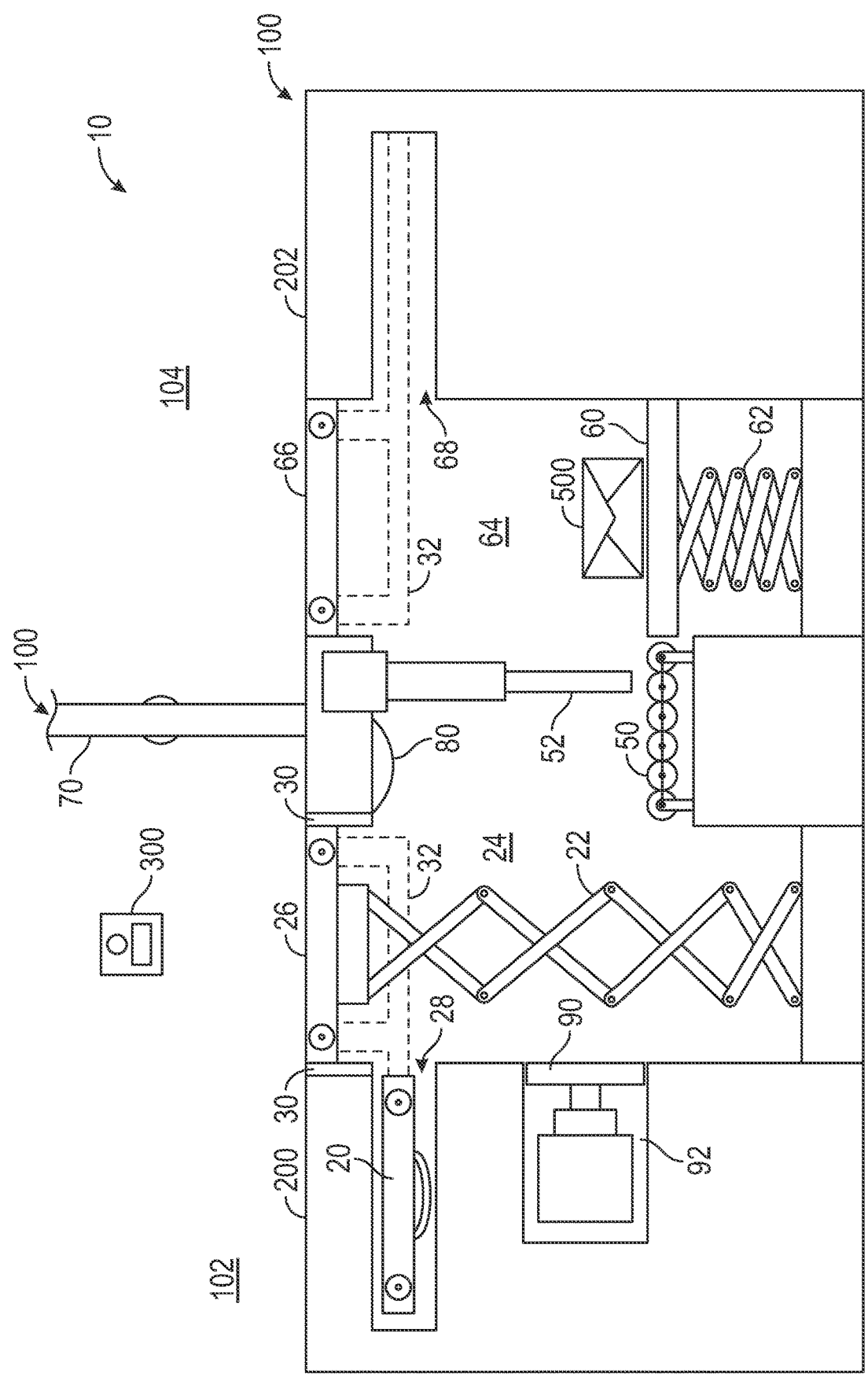
FIG. 10 is a diagrammatic side elevation view depicting an example embodiment of the present invention showing action of the first lifting means engaging with the first cover member to reset the apparatus for conveyance of another delivery. First cover member has now become the receiving area.

FIG. 8 further illustrates action of first lifting means 22 returning to the upper position. Note that receiving area 20 is detached from first lifting means 22 and positioned into recess 28 in lieu of first cover member 26, as described previously. See FIGS. 9 and 10. Once receiving area 20 is disposed interior to recess 28, first lifting means 22 raises to the upper position and engages with first cover member 26. First cover member 26 now serves as receiving area 20 and receiving area 20 now serves as first cover member 26 until cycled out to change positions once again. In this manner, packages delivered shortly after each other are conveyable by the apparatus 10 without the conveyance of one delivery preventing drop off of the other delivery.

Once the secure partition 52 closes whereby the second cavity 64 is secured and closed off from the conveyance 50, second cover member 66 deploys to the retracted position, in this example embodiment in like manner as first cover member 26. See FIG. 11. Second lifting means 62 then raises to the upper position to seat deposit area 60 flushly into flooring 202 interior to the building envelope 100. The delivered item 500 is thence presented for collection by the recipient securely inside the building envelope 100 within building interior 104. See FIG. 12.

Figure 11:
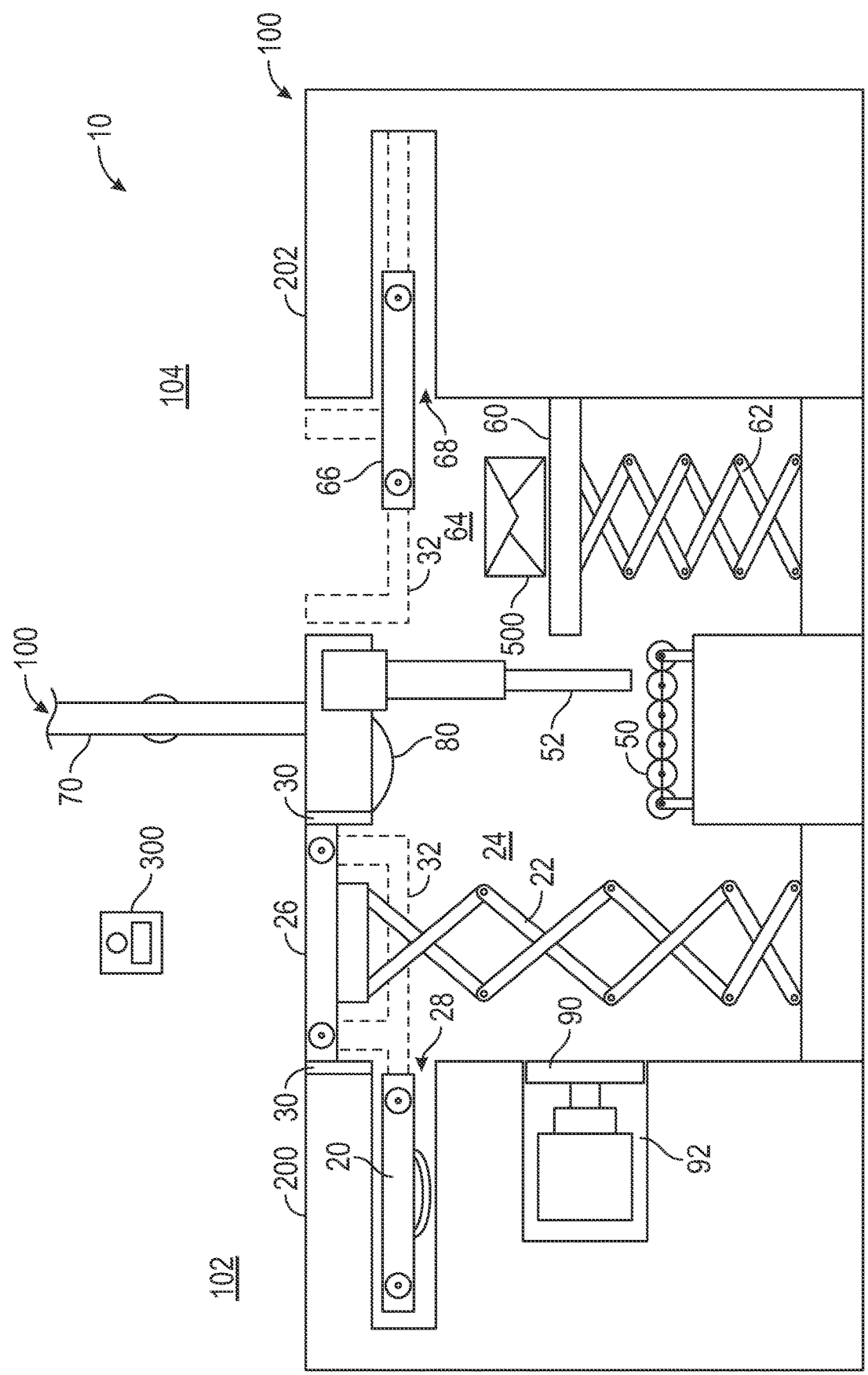
FIG. 11 is a diagrammatic side elevation view of an example embodiment of the apparatus depicting action of a second lifting means raising the delivery toward an upper position. Second cover member is retracted to recess to accommodate conveyance of the delivery to the upper position.
Figure 12:
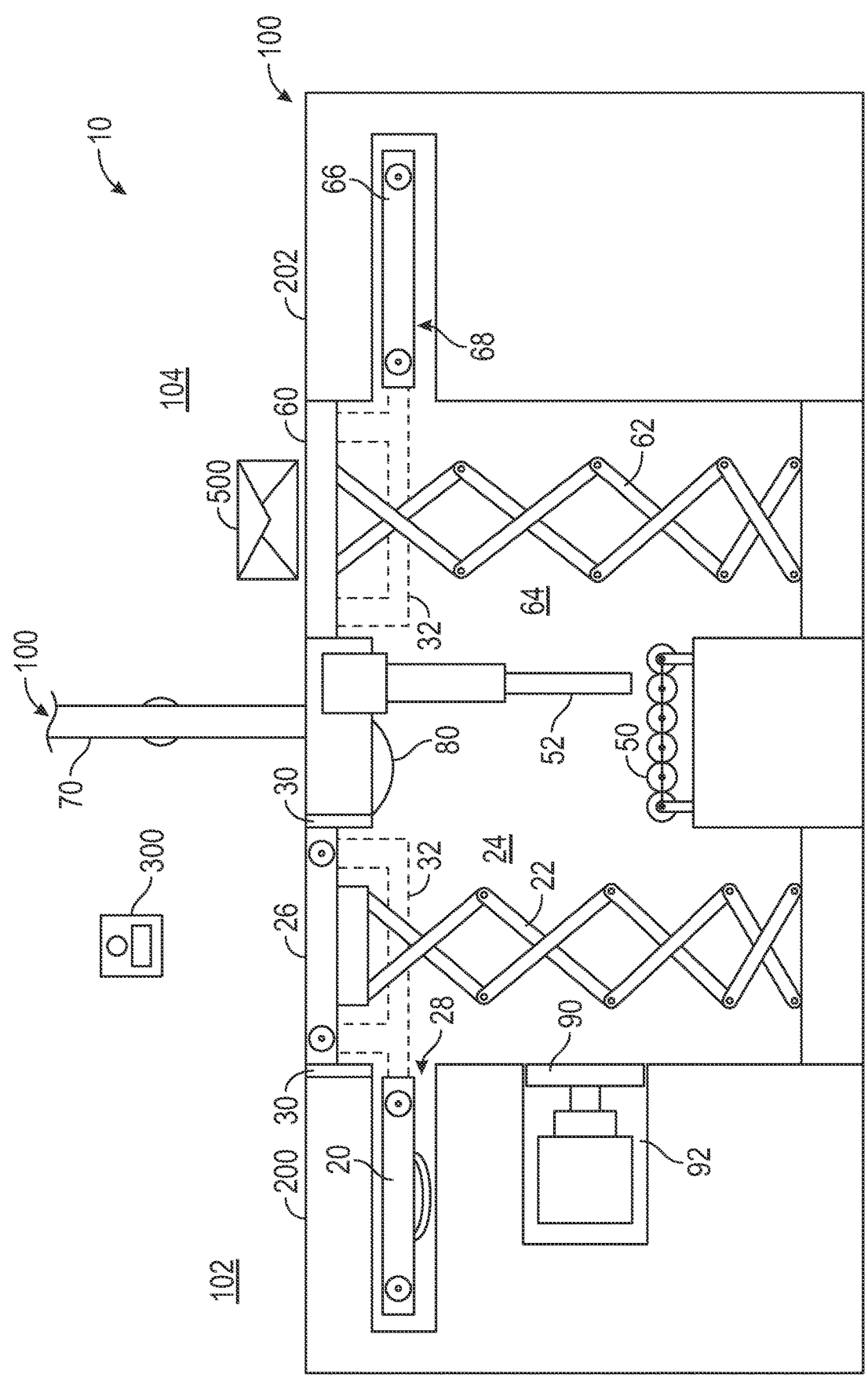
FIG. 12 is a diagrammatic side elevation view or an example embodiment of the apparatus depicting the delivery positioned flush with a flooring interior to the building envelope.
Figure 13:
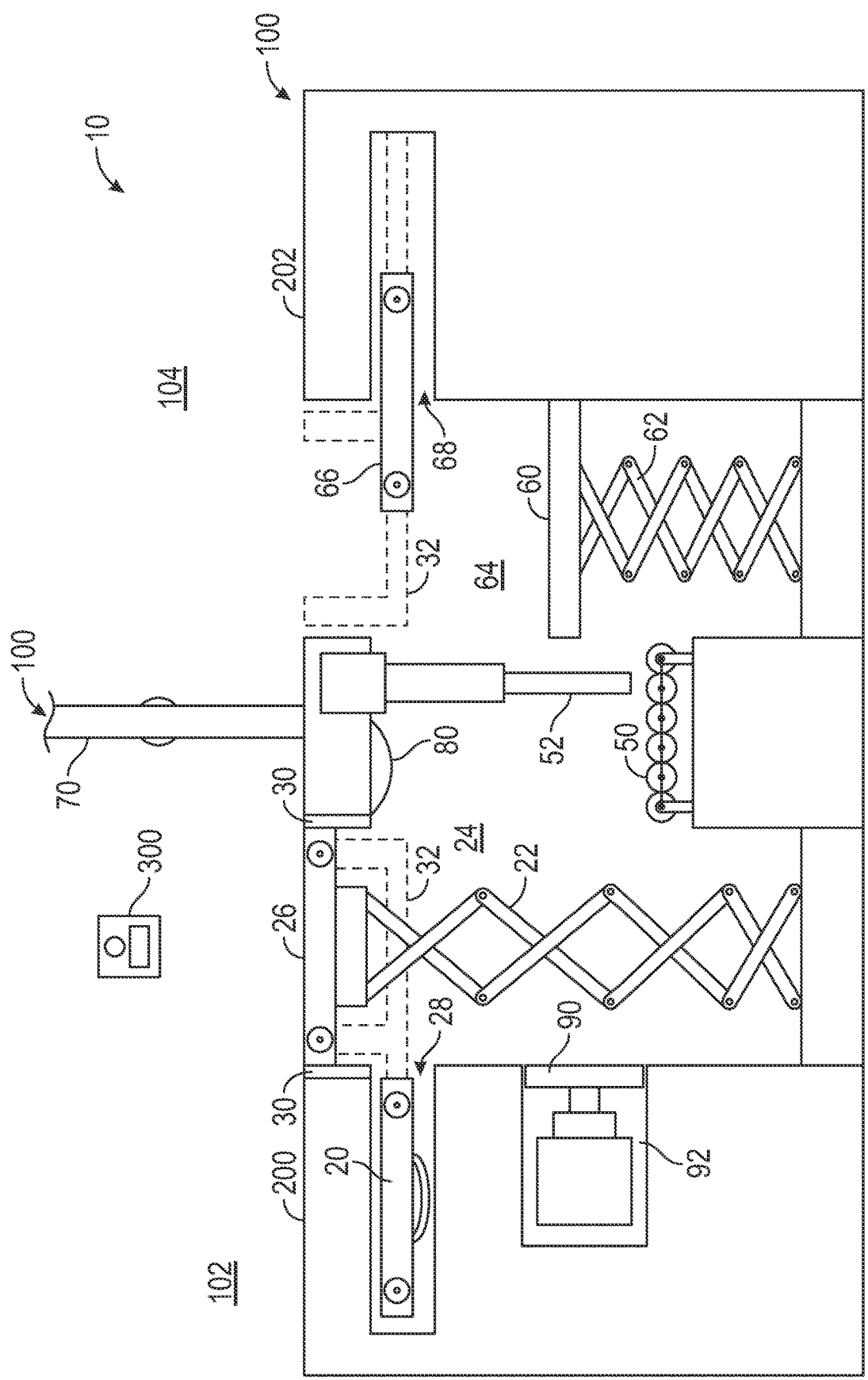
FIG. 13 is a diagrammatic side elevation view of an example embodiment of the apparatus illustrating the second lifting means returning to the lower position after the delivery has been removed from the deposit area interior to the building envelope whereby second cover member is redeployed to enclose the second cavity.
Figure 14:
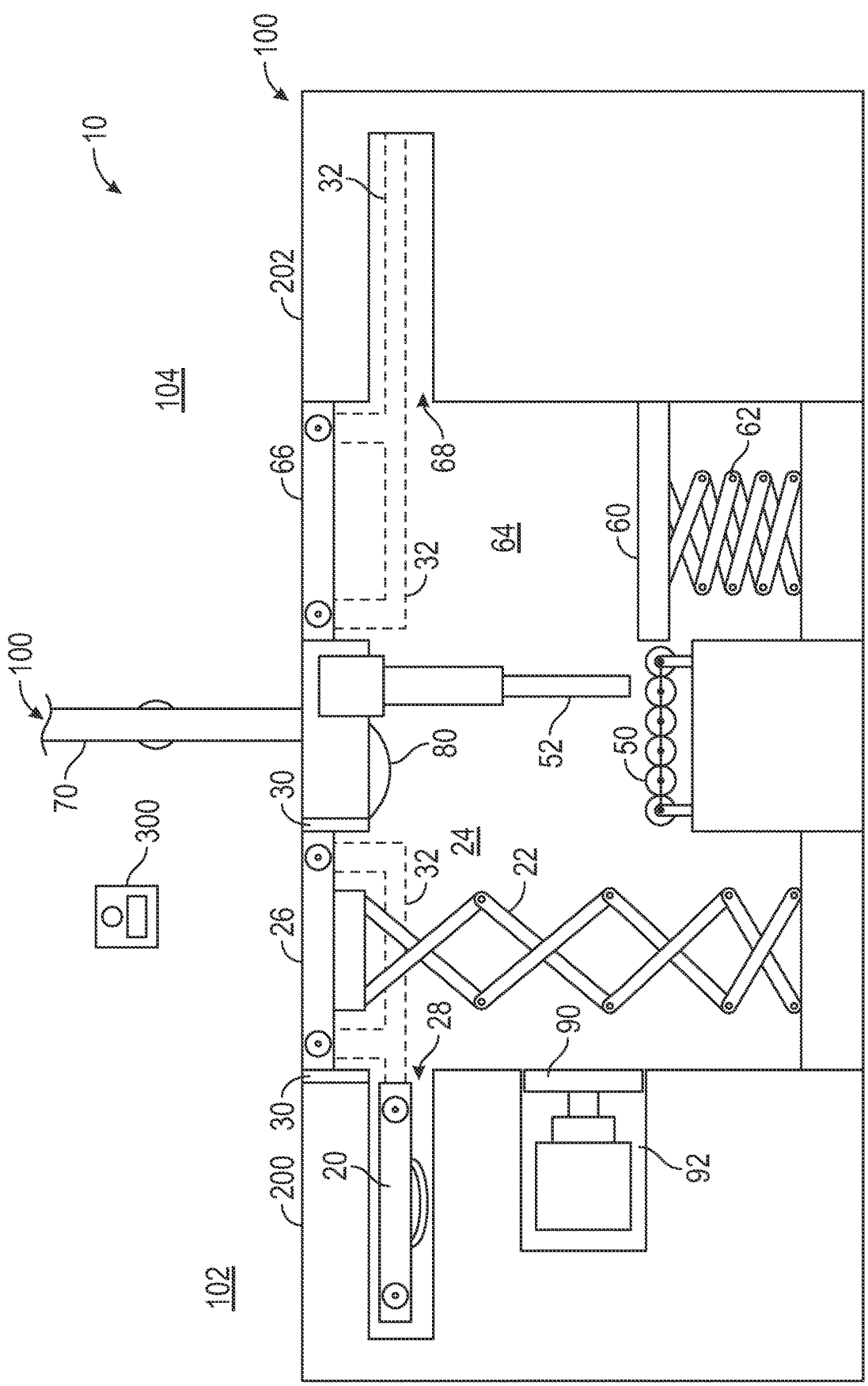
FIG. 14 is a diagrammatic side elevation view of an example embodiment of the apparatus restored to the initial configuration and ready for receipt of another delivery.

FIG. 11 illustrates action of second lifting means 62 within second cavity 60 to raise the deposited delivery 500 up to a floor surface within the building envelope 100. Second cover member 66 deploys into recess 68 to accommodate movement of second lifting means 62 to the upper position. Deposit area 60 is presented flush with ground or floor surface interior to the building envelope 100. See FIG. 12. Once the delivered item 500 is removed from deposit area 60, second lifting means 62 is lowered into the lowered position and second cover member 66 deploys from recess 68 to reseat into the space vacated by the deposit area 60. Initiation of second lifting means 62 from upper position to lower position may be effectuated by sensor (e.g. sensation of mass of delivered item 500 being removed) or may be effectuated manually by action of a switch, for example, or remote control over network.

Once second lifting means 62 has returned to the lowered position in second cavity 64 one full cycle of the apparatus 10 has been effectuated and the apparatus is ready to deliver another package. See FIG. 14.

FIG. 15 illustrates a flow diagram illustrating the various steps undertaken by the apparatus in response to the delivery of an item into the receiving area 20. Sensation of delivered item 500 within receiving area 20 instantiates a signal to initiate the conveyance of the delivered item 500 interior to the building envelope 100 in the manner previously described. The signal may alert a user over network or audibly or visually to manually initiate the conveyance sequence. Alternatively, in some embodiments, automated or programmable action of the apparatus may occur. Sensors contemplated in example of the present invention include registering an object placed within an optical field of view, sensing weight of a delivered item upon the receiving area 20, covering of a light dependent resistor, near field communication between transmitters in the delivered item 500 and receivers (not shown) as part of the apparatus 10, or via internet protocol presenting a signal in response to receipt of a delivery notification as sent by the carrier.

Figure 16:
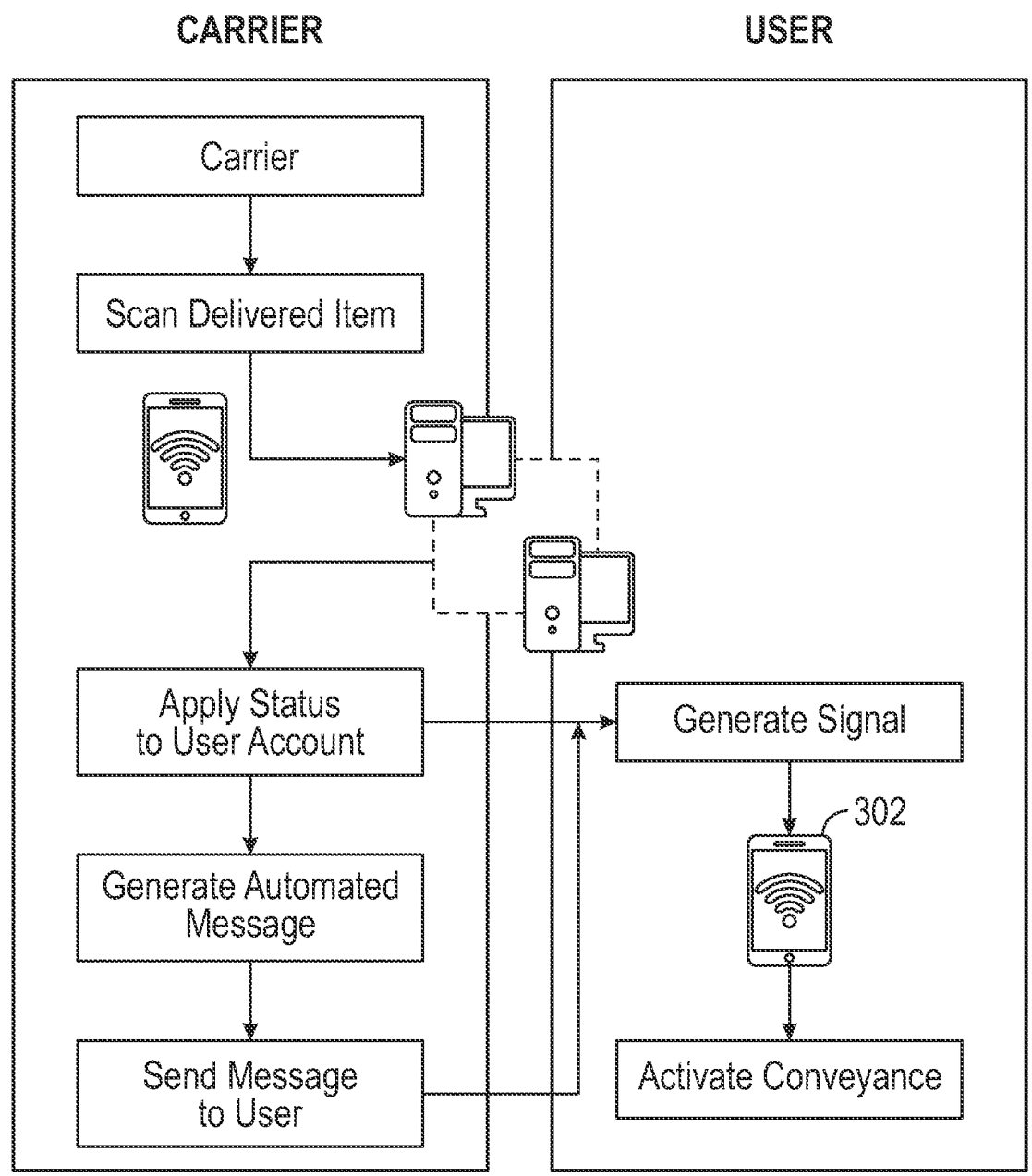
FIG. 16 is a diagrammatic view of a delivery notification effectuated by internet protocol when a delivery notification is sent by the carrier.

FIG. 16 illustrates an example embodiment of internet protocol effectuating notice to a user that a delivered item has been delivered. In such a situation, the apparatus 10 is operable over network (or by manual switch in circuit with the apparatus) to initiate the apparatus.

What is claimed is:

1. An apparatus for conveying delivered items into a building envelope comprising:
   a receiving area exteriorly situated relative to a building envelope, said receiving area adapted to position within a ground space disposed proximal to the entrance to the building;
   a deposit area interiorly situated relative to the building envelope, said deposit area adapted to position within a floor space disposed proximal to the entrance to the building;
   a first cavity disposed underlying the receiving area;
   a second cavity disposed underlying the deposit area;
   a first lifting means disposed within the first cavity, said first lifting means supporting the receiving area wherein the receiving area is lowerable and raisable within the first cavity between an upper and a lower position;
   a second lifting means disposed within the second cavity, said second lifting means supporting the deposit area wherein the deposit area is raisable and lowerable within the second cavity between a lower position and an upper position;
   a conveyance disposed interconnecting the first cavity and the second cavity, said conveyance disposed in adjacent proximity to the lower position of the first and second lifting means whereby items removed to the lower position by the first lifting means are conveyed to the lower position of the second lifting means;
   wherein items placed upon the receiving area may be automatically transported inside the building.

2. The apparatus for conveying delivered items into the building envelop of claim 1 further comprising a delineation of the receiving area devised to be detectable by unmanned aerial vehicles and/or unmanned ground vehicles whereby delivery of items into the delivery area by unmanned vehicle is facilitated.

3. The apparatus for conveying delivered items into the building envelope of claim 1 further comprising a sensor whereby the presence of an item positioned within the receiving area is determinable.

4. The apparatus for conveying delivered items into the building envelope of claim 3 wherein the presence of a delivery is signaled to a peripheral device over network.

5. The apparatus for conveying delivered items into the building envelope of claim 1 wherein an antimicrobial agent is directable at the item when the item is moved through the first cavity, the conveyance, and/or the second cavity.

6. The apparatus for conveying delivered items into the building envelope of claim 5 wherein the antimicrobial agent comprises directed application of ultraviolet light.

7. The apparatus for conveying delivered items into the building envelope of claim 5 further comprising a secure partition moveable to enclose and alternatively open at least the second cavity with respect to at least the first cavity.

8. The apparatus for conveying delivered items into the building envelope of claim 1 further comprising a forcing means configured to move the item from the receiving area onto the conveyance and thence to the deposit area.

9. The apparatus for conveying delivered items into the building envelope of claim 8 wherein the forcing means is an extendible arm extendible into the first cavity from a retracted position to an extended position, wherein movement of the extendible arm from the retracted position to the extended position presents a contact member from immediate proximity with the receiving area to immediate proximity with the deposit area when said receiving area and deposit area are disposed in the lower positions, whereby the extendible arm translocates items disposed upon the receiving area to the deposit area by way of the conveyance.

10. The apparatus for conveying delivered items into the building envelope of claim 8 wherein movement of a delivery from the receiving area to the deposit area is effectuated in response to a stimulus.

11. The apparatus for conveying delivered items into the building envelope of claim 10 wherein the stimulus is selected from the group consisting of:
   visual identification of a package by means of a camera;
   weight of the package upon the receiving area; or
   operation by switch.

12. The apparatus for conveying delivered items into the building envelope of claim 11 wherein the switch is operable over network.

13. The apparatus for conveying delivered items into the building envelope of claim 1 further comprising a first cover member moveable between a retracted position and an engaged position, said first cover member disposed to position into the engaged position and fill the space vacated by the receiving area when the first lifting means is not disposed in the upper position, said first cover member retractable into the retracted position interior to a recess immediately proximal to the first cavity when the first lifting means is disposed in the upper position.

14. The apparatus for conveying delivered items into the building envelope of claim 13 further comprising a second cover member moveable between a retracted position and an engaged position, said second cover member disposed to position into the engaged position and fill the space vacated by the deposit area when the second lifting means is not disposed in the upper position, said second cover member retractable into the retracted position interior to a recess immediately proximal to the second cavity when the second lifting means is disposed in the upper position.

15. The apparatus for conveying delivered items into the building envelope of claim 13 wherein the first cover member maintains position in the space vacated by the receiving area and, after conveyance of the delivered item to the deposit area, the receiving area detaches from the first lifting means en route to the upper position wherein said receiving area positions into the recess and the first lifting means thence attaches to the first cover member whereby the receiving area and first cover member alternate positions and cycle between said alternate positions.

16. The apparatus for conveying delivered items into the building envelope of claim 15 further comprising a sensor whereby the presence of an item positioned within the receiving area is determinable.

17. An apparatus for conveying delivered items into a building envelope comprising:
- a receiving area exteriorly situated relative to a building envelope, said receiving area adapted to position within a ground space disposed exterior and proximal to the entrance to the building;
- a deposit area interiorly situated relative to the building envelope, said deposit area adapted to position within a floor space disposed interior and proximal to the entrance to the building;
- a first cavity disposed underlying the receiving area;
- a second cavity disposed underlying the deposit area;
- a first lifting means disposed within the first cavity, said first lifting means supporting the receiving area wherein the receiving area is lowerable and raisable within the first cavity between an upper position and a lower position;
- a second lifting means disposed within the second cavity, said second lifting means supporting the deposit area wherein the deposit area is raisable and lowerable within the second cavity between a lower position and an upper position;
- a conveyance disposed interconnecting the first cavity and the second cavity, said conveyance disposed in adjacent proximity to the lower position of the first and second lifting means wherein the conveyance is aligned with the receiving area and the deposit area when each of the first and second lifting means is disposed at the lower position;
- an extendible arm disposed extendible from within a recess opening into the first cavity, said extendible arm moveable from a retracted position interior to the recess to an extended position wherein movement of the extendible arm from the retracted position to the extended position presents a contact member from an immediate proximity with the receiving area to an immediate proximity with the deposit area, when said receiving area and deposit area are disposed in the lower positions;
- a first cover member moveable between a retracted position and an engaged position, said first cover member disposed to position into the engaged position and fill the space vacated by the receiving area when the first lifting means is not disposed in the upper position, said first cover member retractable into the retracted position interior to a recess immediately proximal to the first cavity when the first lifting means is disposed in the upper position; and
- a second cover member moveable between a retracted position and an engaged position, said second cover member disposed to position into the engaged position and fill the space vacated by the deposit area when the second lifting means is not disposed in the upper position, said second cover member retractable into the retracted position interior to a recess immediately proximal to the second cavity when the second lifting means is disposed in the upper position;
- wherein items placed upon the receiving area may be automatically transported inside the building.

18. The apparatus for conveying delivered items into the building envelope of claim 17 further comprising a secure partition moveable to enclose and alternatively open at least the second cavity with respect to at least the first cavity.

19. The apparatus for conveying delivered items into the building envelope of claim 17 wherein movement of the item from the receiving area to the deposit area is effectuated in response to a stimulus.

20. The apparatus for conveying delivered items into the building envelope of claim 19 wherein the stimulus is selected from the group consisting of:
- visual identification of the item by means of a camera;
- weight of the item upon the receiving area; and
- operation by remote switch.

21. The apparatus for conveying delivered items into the building envelope of claim 20 wherein the presence of the item is signaled to a peripheral device over network.

22. The apparatus for conveying delivered items into the building envelope of claim 20 wherein the remote switch is operable over network.

23. The apparatus for conveying delivered items into the building envelope of claim 22 wherein an antimicrobial agent is directable at the item when the item is moved through the first cavity, the conveyance, and/or the second cavity.

24. The apparatus for conveying delivered items into the building envelop of claim 22 further comprising a delineation of the receiving area devised to be detectable by unmanned aerial vehicles and/or unmanned ground vehicles whereby delivery of items into the delivery area by unmanned vehicle is facilitated.

25. The apparatus for conveying delivered items into the building envelope of claim 24 wherein the antimicrobial agent comprises directed application of ultraviolet light.

* * * * *